United States Patent [19]

Howard

[11] 4,064,234

[45] Dec. 20, 1977

[54] METHODS AND PHARMACEUTICAL PREPARATION FOR THE TREATMENT OF HYPERCHOLESTEROLEMIA

[75] Inventor: Alan N. Howard, Cambridge, England

[73] Assignee: Bristol-Myers Company, New York, N.Y.

[21] Appl. No.: 744,909

[22] Filed: Nov. 26, 1976

Related U.S. Application Data

[63] Continuation-in-part of Ser. No. 583,308, June 2, 1975, Pat. No. 4,041,153.

[30] Foreign Application Priority Data

June 4, 1974 United Kingdom ............... 24794/74

[51] Int. Cl.$^2$ .................... A61K 33/08; A61K 33/10; A61K 31/235; A61K 31/19

[52] U.S. Cl. .................................... 424/157; 424/154; 424/156; 424/308; 424/317

[58] Field of Search ............... 424/154, 157, 156, 317, 424/308

[56] References Cited

PUBLICATIONS

Laboratorios Hosbon — Chem. Abst., vol. 83 (1975) p. 58440x.
Laboratoires Vifor — Chem. Abst., vol. 67 (1967) p. 2899g.
Uriach — Chem. Abst., vol. 79 (1973) p. 136,816j.

*Primary Examiner*—Sam Rosen
*Attorney, Agent, or Firm*—David M. Morse

[57] ABSTRACT

A composition for treatment of hypercholesterolemia contains clofibrate or a clofibrate derivative, a magnesium or aluminum ion contributing compound which forms substantially insoluble metal bile acid salts and, optionally, a basic anion exchange resin. The composition components combine to give synergistic effect.

16 Claims, No Drawings

METHODS AND PHARMACEUTICAL PREPARATION FOR THE TREATMENT OF HYPERCHOLESTEROLEMIA

CROSS-REFERENCE TO RELATED APPLICATION

This is a continuation-in-part application of co-pending application Ser. No. 583,308 filed June 2, 1975, now U.S. Pat. No. 4,041,153.

The present invention relates to methods and pharmaceutical preparations for the treatment of hypercholesterolaemia.

It has long been recognized that certain conditions or diseases, such as coronary heart disease and atherosclerosis, are associated with and may be caused by the presence of too high a level of cholesterol in the blood plasma; and for the treatment of such condition many attempts have been made to find means for reducing the cholesterol level in blood plasma, for instance by provision of some kind of orally-administerable pharmaceutical preparation capable of exerting a hypocholesterolaemic effect, that is to say reducing the cholesterol level in blood plasma and thus combating hypercholesterolaemia.

It has now been found that, from amongst the wide variety of preparations, both in the nature of drugs and other products, which have hitherto been employed for the reduction of blood-cholesterol levels, it is possible to select combinations which exhibit a quite unexpectedly enhanced or synergistic effect, as will be described hereinafter. The selected combinations which display this peculiar and valuable therapeutic property are formed between certain known synthetic blood cholesterol-reducing drugs and certain metallic compounds. Although it is known that some of the latter can also reduce blood cholesterol, what is surprising is that when used in combination they can quickly achieve, in at least a large proportion of patients suffering from hypercholesterolaemia, a reduction in blood cholesterol which is greater than can be hoped for with one of the synthetic blood cholesterol-reducing drugs alone and also faster than could be expected with one of the metallic compounds alone, or even both of them jointly. The use of this synergistic combination of blood cholesterol-reducing agents thus opens the way to significant improvements in the treatment of hypercholesterolaemia.

The combination needed to attain these remarkable results is formed by the administration per os in a certain ratio (if appropriate separately but for convenience preferably in admixture) of both a. a hypocholesterolaemic compound selected from p-chlorophenoxyisobutyric acid, the methyl, ethyl, propyl or butyl ester thereof or a sodium, potassium, calcium, magnesium, aluminum, zinc, bismuth or iron salt thereof, and b. one or more ingestible non-toxic aluminum or magnesium salts capable of dissolution in human gastrointestinal juices, the total amount of non-toxic metal being from 3.2 to 90 equivalents per mole of p-chlorophenoxyisobutyric acid or ester or salt thereof.

According to one aspect of the invention there is therefore provided a method for the treatment of hypercholesterolaemia, in which there is administered to the patient per os a hypocholesteremic effective dose of a pharmaceutical composition comprising a. a compound selected from p-chlorophenoxyisobutyric acid, the methyl, ethyl, propyl or butyl ester thereof or a sodium, potassium, calcium, magnesium, aluminum, zinc, bismuth or iron salt thereof, and b. an ingestible non-toxic aluminum or magnesium salt capable of dissolution in human gastrointestinal juices, the total amount of non-toxic metal being from 3.2 to 90 equivalents per mole of p-chlorophenoxyisobutyric acid or ester or salt thereof.

In calculating the ratio of metal to p-chlorophenoxyisobutric acid derivative, the equivalent weights of the metals are to be taken as the equivalents of the metals in the valency states in which they react with the bile acids and one mole of a di- or trivalent metal salt of the p-chlorophenoxyisobutyric acid derivative is to be counted as two or three moles of said derivative.

As previously indicated, although not absolutely necessary it is highly convenient to administer both the p-chlorophenoxyisobutyric acid derivative and also the metallic compound(s) simultaneously in the form of a simple admixture or formulated into some other, more sophisticated, pharmaceutical preparation and this invention will in the main be hereinafter described in terms of such preparation.

Thus, in another and more important aspect, this invention provides pharmaceutical formulations, for use in the treatment per os of hypercholesterolaemia, which comprise a. a hypocholesteremic effective amount of a compound selected from p-chlorophenoxyisobutyric acid, the methyl, ethyl, propyl or butyl ester thereof or a sodium, potassium, calcium, magnesium, aluminum, zinc, bismuth or iron salt thereof, and b. an ingestible non-toxic aluminum or magnesium salt capable of dissolution in human gastrointestinal juices, the total amount of non-toxic metal being from 3.2 to 90 equivalents per mole of p-chlorophenoxyisobutyric acid or ester or salt thereof, either alone or in combination with a pharmaceutical vehicle.

Experience has so far indicated that the most preferred of the component (a) synthetic organic blood cholesterol-reducing drugs for use in accordance with this invention are p-chlorophenoxyisobutyric acid and its derivatives, especially its ethyl ester (known as "Clofibrate"), and its salts. The most exhaustive tests have been undertaken with these blood cholesterol-reducing drugs, and their excellent activity in accordance with this invention recommends their use, as will be apparent hereinafter.

As regards the ingestible non-toxic aluminum or magnesium compounds for use in this invention, one may employ any ingestible oxide, hydroxide or non-toxic salt of these metals which is capable of dissolution in the gastrointestinal juices of the patient, so as there to yield a corresponding salt or ion capable of reaction with bile acids to form insoluble salts which can be excreted in the faeces. The choice of such metal compounds is of course wholly within the competence of anyone with knowledge concerning pharmaceutical formulations, and can therefore be left to them. Suitable aluminium compounds are the oxide, hydroxide, chloride, phosphate, sulphate, silicate, stearate and carbonate, whilst suitable magnesium compounds are the oxide, hydroxide, aluminate, carbonate, silicate, chloride, citrate, phosphate, lactate, stearate and sulphate.

The metallic salts may be administered in any convenient form, either solid or (where possible) liquid, but will normally be used most readily in the form of fine particles or powder, sieved to eliminate any oversize material, and where appropriate then agglomerated — when desired, after admixture with the cholesterol-reducing drugs — and filled into capsules or compressed into tablets.

It is however essential, if the desired results are to be attained, for the ratio of the metallic compounds used in accordance with this invention to be kept within the range, relative to the component (a) blood cholesterol-reducing drugs of from 3.2 to 90 equivalents of metal per mole. Thus the proportion of aluminum or magnesium exceeds the stoichiometric amount in which the aluminum or magnesium combines with the blood cholesterol-reducing drug of component (a) — if in free acid form — to build the corresponding aluminum or magnesium salt of the drug. The use of such aluminum or magnesium metal salts of the blood cholesterol-reducing drug(s) of component (a) is within the scope of this invention but only so long as sufficient additional aluminum or magnesium compound(s) are present to bring the ratio up to at least 3.2 equivalents per mole; the use of the aluminum or magnesium metal salt alone without such an excess-forming addition, does not make it possible to attain the desired enhanced results.

The upper limit of about 90 equivalents of metal per mole is quite a practical limit. In fact, the upper level is determined by the daily dosage of metal which can be administered to the patient without inducing severe side-effects. This maximal daily dosage is varying from metal to metal. For guidance a daily dosage of 10 g. of aluminum or 5 g. of magnesium is held to be the upper level that may be administered.

In fact, not merely a small excess of metal but a relatively large one is needed if one is to secure optimum results. As will be demonstrated hereinafter, the admixture of the blood cholesterol-reducing drug of component (a) with the metallic compound has a synergistic effect in the reduction of cholesterol values in human plasma, which is useful over the entire molar range of proportions of from 3.2 to 90 equivalents per mole but to obtain the maximum advantage from the invention it is preferred to use mixtures in the proportions of from 4 to 40 equivalents per mole and more especially of from 4 to 20 equivalents per mole. In fact, the most preferred ratio is substantially 4 to 15 equivalents per mole.

As will be obvious, for special purposes flavouring materials (such as orange oil) and synthetic sweeteners (such as saccharine and saccharine sodium) may be added to the individual drug(s) and/or metallic compound(s), as can also edible colouring matters and/or carriers and/or faecial softeners and/or surfactants.

For certain purposes it may be useful to add certain other drugs to potentiate the hypocholesterolaemic action of the combination. Lipolytic compounds such as poly-unsaturated phosphatidyl choline obtained from soya are particularly beneficial in this respect.

A particularly excellent hypocholesterolaemic effect is achieved if in addition to a metallic salt and compound of component (a), an anion exchange resin is employed in the compositions for use in this invention. Preferably, the total amount of anion exchange resin employed in the compositions is from 50 to 8000 g. per mole and most preferably from 150 to 3000 g. per mole, of the compound of component (a).

Any type of basic non-toxic anion exchange resin may be used in the compositions of the present invention. The resin can be, for example, a water-in soluble synthetic polymer or a polysaccharide substituted with amino groups (which may be quaternised). The products may be cross-linked or non-cross-linked.

One particularly preferred type of resin is the $\omega$-dialkylaminoalkyl, $\omega$-aminoalkyl, $\omega$-guanidinoalkyl and the $\omega$-(para-aminophenyl)alkyl ethers of polysaccharides (which may be cross-linked or non-cross-linked) and their derivatives, and the non-toxic salts formed by such ethers with acids. The preferred polysaccharide bases of these resins are dextran cross-linked with epichlorohydrin or cellulose, and the preferred ethers are those in which the or each alkyl group contains from 1 to 4 carbon atoms. The preferred dextrans are the anhydroglucose polymers produced by the action of various strains of Leuconostoc upon aqueous solutions of sucrose, and the water-insoluble cross-linked dextrans produced by the action of bifunctional compounds upon water-soluble dextrans (such as the resins described in U.S. Pat. No. 3,042,667). Cross-linked water-insoluble celluloses are produced by the same methods. Desirably, the amino-alkyl groups in the resins are the 2-diethylaminoethyl, aminoethyl guanidinoethyl and p-aminobenzyl groups. Such compounds are for example described in U.S. Pat. No. 3,277,025. The preferred salts of these compounds are the hydrochlorides.

Another preferred type of basic non-toxic anion exchange resin which may be used in the compositions of the invention is the water-insoluble high molecular weight reaction products obtained by reaction of a polyalkylene polyamine with epichlorohydrin and/or glycerol-1,3-dichlorohydrin and/or an aliphatic bis-epoxy compound (such as 1,2:3,4-bis-epoxybutane, bis-epoxypropyl ether or a bis-epoxypropyl ether of an $\alpha$, $\omega$-alkylene glycol. The preferred polyalkylene polyamines for use in the reaction are the polyethylene polyamines such as triethylenetetramine, tetraethylenepentamine and pentaethylenehexamine: such compounds contain at least as many secondary amino groups as primary amino groups in the molecule. Desirably, in the reaction products a proportion of the amino groups are quaternised and form chloride salts; this is conveniently done by bringing the co-polymer to pH4 with HCl and drying it.

A third preferred type of basic non-toxic anion exchange resin which may be used in the compositions of the inventiom is those resins formed by polymerisation of an ethylenically unsaturated monmer containing at least one amino group, the amino groups in the resin being quaternised. Such resins may be prepared either by polymerising a pre-quaternised monomer or by first polymerising an unquaternised monomer and then quaternising the resultant product. The ethylenically-unsaturated monomer is desirably a compound of the general formula:

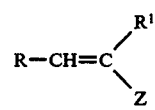

(in which
R is a hydrogen atom or a methyl, phenyl, carboxy, carboxymethyl or carboxyethyl group;
$R^1$ is a hydrogen atom, a methyl group or a group of the formula —$CH_2COOX$ in which X is a hydrogen atom or an alkyl group having one to four carbon atoms; and Z is a pyridinium or carboxylic ester grouping which is free from aliphatic unsaturation and which contains a quaternary ammonium group, for example a carboxyalkyl group terminated by a quaternary alkylammonium group).

Preferred monomers are vinylpyridine, α-methylvinylpyridine and the acrylic, methacrylic, crotonic, cinnamic and α-methylcinnamic esters of the ω-dialkylaminoalkanols in which each of the N-alkyl groups contains not more than four carbon atoms. The quaternization of the amino groups before or after polymerisation may be effected by reaction with an alkyl halide, a dialkyl sulphate or a trialkyl phosphate. In order to secure adequate spacing of the quaternary groups this third group of anion exchange resins conveniently incorporate one or more ethylenically-unsaturated monomers which are free from amino groups, that is they are conveniently copolymers between an amino-bearing monomer and a monomer which does not contain amino-groups. Depending upon the nature of the non-amino comonomer or comonomers used these resins may be of an essentially linear structure or may be cross-linked. When a linear copolymer is to be produced the copolymerizing monomer should be a monoethylenic monomer free from groups which could interfere with the basic action of the quaternary amino groups in the final polymer, that is free from ionizable groups and hydrophobic groups. Examples of suitable non-amino monomers for use in this class of resins are alkyl methacrylates in which the alkyl group contains one to four carbon atoms (such as methyl methacrylate), monocyclic aromatic hydrocarbons and halohydrocarbons containing a vinylidene group such as styrene, α-methylstyrene and ω-chlorostyrene, vinyl alkanoates having one to four carbon atoms in the alkanoate group (such as vinyl acetate) and ethylenically-unsaturated nitriles (such as acrylonitrile and methacrylonnitrile). Such non-amino monomers are preferably used in an amount not exceeding 50% of the weight of the amino-containing monomer.

Alternatively or additionally, the resin may be one made by polymerising the amino-containing monoethylenically unsaturated monomer with not more than 20% (based upon the total weight of all the co-monomers), of a monomer which is free from ionizable groups and contains at least two ethylenically-unsaturated groups. Examples of such monomers are methylene bis-acrylamide and bis-methacrylamide, alkylene glycol bis-acrylates and alkylene bis-methacrylates (such as ethylene bis (methacrylate)), the divinyl monocyclic aromatic hydrocarbons (such as divinylbenzene), the tris(alkenylamines (such as triallylamine) and polyalkenylated polyols or sugars (such as triallylpentaerythritol and polyallyl sucrose). Whether or not either type of comonomer is employed, the polymerisation is conveniently effected in an aqueous or alcoholic medium in the presence of a catalyst (such as a permonosulphate, perbenzoic acid or an azo compound such as azobis(isobutyronitrile) which acts as a source of free radicals.

A fourth preferred type of basic non-toxic anion exchange resin for use in the compositions of the present invention is a styrene polymer substituted with basic groups. Such a resin may be made by copolymerizing styrene with a minor proportion (preferably not more than 5% by weight) of divinylbenzene. The resulting copolymer is then chloromethylated and the product treated with a tertiary amine, preferably a trialkylamine containing not more than 10 carbon atoms, so as to introduce quaternary ammonium groups. The extent of chloromethylation and hence the proportion of quaternary groups can be varied over quite wide limits.

Amongst the above mentioned resins, it has been found that particularly good results have been obtained with the diethylaminoethyl celluloses and dextrans, especially with the product (Secholex (PDX chloride or poly-[2-(diethylamino)ethyl]-polyglycerylene dextran hydrochloride). Cholestyramine (which is a cross-linked styrene polymer containing tertiary amino groups) and colestipol (which is a polyethylene polyamine-epichlorohydrin condensation product) are also very effective.

The most preferred resins are cholestyramine, colestipol or poly-[2-diethylamino)ethyl]-polyglycerylene dextran hydrochloride.

The treatment in accordance with this invention may be carried out along conventional lines, in the sense that the daily doses of the cholesterol-reducing drug of component (a) and the metallic compound which are administered, either separately or in conjunction with one another, should in accordance with this invention be more or less the same as the respective amounts in which they have individually been administered in accordance with conventional therapeutic practice.

Thus for instance, when the blood cholesterol-reducing drug of component (a) employed is ethyl parachlorophenoxyisobutyrate (clofibrate) the normal conventional dose is 1.5–2.5 g./day, and the dose cannot be increased above this 2.5 g./day upper limit without danger of gastrointestinal side effects. When an anion exchange resin is also employed the normal conventional dose of such a resin is 3–40 g./day. Examples of suitable doses of metal salts are 2.4 g./day of magnesium hydroxide or aluminum hydroxide.

In order further to demonstrate the remarkable therapeutic results attainable in accordance with this invention, the results of certain clinical trials will be reported below. At this point it should be noted that a certain number of the patients tested, but only quite a small percentage, appeared to be resistant to the blood cholesterol-reducing agents employed (which is common clinical experience in the case of blood cholesterol-reducing agents) and with such patients naturally no significant effect could be observed. To maintain accuracy, the results obtained with such patients have therefore been eliminated from the clinical test results reported below:

Effect of clofibrate and metallic ions on serum cholesterol in patients

Procedure

Patients were selected with a serum cholesterol of greater than 235 mg./100 ml. Following three baseline determinations they were randomly allocated to the following treatments:

a. Clofibrate (Atromid-S) 1.5 g./day,
b. Clofibrate 1.5 g./day + aluminum hydroxide 2.4 g./day,
c. Clofibrate 1.5 g./day + magnesium hydroxide 2.4 g./day,
d. Magnesium hydroxide 2.4 g./day,
e. Aluminum hydroxide 2.4 g./day.

Treatment was for 4 weeks in each case, followed by 4 weeks placebo, before continuing with a different treatment. Divided doses were given thrice daily.

Serum cholesterol was analysed by the autoanalyser using the Zak reaction.

Results

The results of the tests are shown in Tables I and II below.

Effect of a combination of PDX chloride, clofibrate and metallic salts

Twelve patients with hypercholesterolaemia were treated placebo for three months and then with a combi-

TABLE I

Effect of Clofibrate and Magnesium Hydroxide Alone and in Combination on Serum Cholesterol

| PATIENT NO. | CLOFIBRATE Cholesterol level in mg./100 ml. | | | MAGNESIUM HYDROXIDE Cholesterol level in mg./100 ml. | | | CLOFIBRATE-MAGNESIUM HYDROXIDE COMBINATION Cholesterol level in mg./100 ml. | | |
|---|---|---|---|---|---|---|---|---|---|
| | Initial | Final | % change (decrease) | Initial | Final | % change (decrease) | Initial | Final | % change (decrease) |
| 2 | 258 | 240 | 7 | 253 | 260 | −3 | 248 | 205 | 17 |
| 10 | 250 | 243 | 3 | 255 | 260 | −2 | 245 | 203 | 17 |
| 13 | 245 | 207 | 16 | 250 | 240 | 4 | 245 | 183 | 25 |
| 16 | 305 | 290 | 5 | 295 | 300 | −2 | 305 | 270 | 11 |
| | | AVERAGE | 8 | | AVERAGE | ~0 | | AVERAGE | 18 |

Predicted Additive Effect = ~8 mg./100 ml.
Actual Effect = ~125% increase over additive effect

TABLE II

Effect of Clofibrate and Aluminum Hydroxide Alone and in Combination on Serum Cholesterol

| PATIENT NO. | CLOFIBRATE Cholesterol level in mg./100 ml. | | | ALUMINUM HYDROXIDE Cholesterol level in mg./100 ml. | | | CLOFIBRATE-ALUMINUM HYDROXIDE COMBINATION Cholesterol level in mg./100 ml. | | |
|---|---|---|---|---|---|---|---|---|---|
| | Initial | Final | % change (decrease) | Initial | Final | % change (decrease) | Initial | Final | % change (decrease) |
| 1 | 280 | 225 | 20 | 290 | 295 | −2 | 280 | 190 | 32 |
| 2 | 258 | 240 | 7 | 260 | 253 | 3 | 245 | 215 | 12 |
| 5 | 253 | 210 | 17 | 263 | 265 | −1 | 245 | 185 | 24 |
| 6 | 240 | 200 | 17 | 270 | 267 | 1 | 253 | 190 | 25 |
| 14 | 290 | 235 | 19 | 298 | 305 | −2 | 290 | 205 | 29 |
| | | AVERAGE | 16 | | AVERAGE | ~0 | | AVERAGE | 24 |

Predicted Additive Effect = ~16 mg./100 ml.
Actual Effect = ~50% increase over additive effect Comments The results of the above tests show that the combination of clofibrate and a non-toxic aluminum or magnesium salt produces on the same patients an average serum cholesterol reduction substantially greater than that afforded by adding the individual effects obtained with the components of the combination.

nation of PDX chloride (15 g./day) and clofibrate (1.5 g./day) for a further three months. The addition of metallic salts to the treatment was then made to seven of the twelve patients as shown in Table III, while the remaining five patients received no additional treatment. Serum cholesterol estimations were carried out on the patients each month.

Results

As shown in Table III, the addition of magnesium and aluminum salts gave a further significant decrease in serum cholesterol, while those patients without such supplementation remained unchanged.

TABLE III

Effect of combinations of metallic cations, Clofibrate and PDX chloride

| Patient No. | 1 S.Ch. | | 2 S.Ch. | | 3 S.Ch. | | 4 S.Ch. | | 5 S.Ch. | | 6 S.Ch. | |
|---|---|---|---|---|---|---|---|---|---|---|---|---|
| PL | | 320 | PL | 250 | PL | 245 | PL | 293 | PL | 385 | PL | 506 |
| | | 315 | | 273 | | 293 | | 255 | | 370 | | 520 |
| | | 300 | | 278 | | 2763 | | 253 | | 368 | | 500 |
| S+A | | 255 | S+A | 180 | S+A | 193 | S+A | 197 | S+A | 300 | S+A | 360 |
| | | 240 | | 177 | | 183 | | 173 | | 285 | | 375 |
| | | 240 | | 183 | | 210 | | 180 | | 280 | | 350 |
| S+A+ Mg | | 220 | S+A+ Mg | 158 | S+A+ Mg | 197 | S+A+ Mg | 168 | S+A+ Mg | 290 | S+A+ Mg | 345 |
| | | 243 | | 185 | | 205 | | 197 | | 295 | | 325 |
| | | 260 | | 168 | | 183 | | 165 | | | | 307 |
| | | 225 | | | | 215 | | 187 | | | | 363 |
| | | 270 | | | | 195 | | 155 | | | | 345 |
| | | 215 | | | | | | | | | | 345 |
| | | | | | | | | | | | S+A+Mg/ | 287 |

| Patient No. | 7 S.Ch. | | 8 S.Ch. | | 9 S.Ch. | | 10 S.Ch. | | 11 S.Ch. | | 12 S.Ch. | |
|---|---|---|---|---|---|---|---|---|---|---|---|---|
| PL | | 500 | PL | 620 | PL | 430 | PL | 350 | PL | 300 | PL | 275 |
| | | 520 | | 520 | | 425 | | 375 | | 280 | | 270 |
| | | 500 | | 595 | | 450 | | 355 | | 295 | | 260 |
| S+A | | 387 | S+A | 325 | S+A | 320 | S+A | 300 | S+A | 205 | S+A | 195 |
| | | 367 | | 327 | | 315 | | 295 | | 195 | | 190 |
| | | 343 | | 330 | | 335 | | 295 | | 210 | | 180 |
| | | | S+A+ Al | | S+A | 330 | S+A | 305 | S+A | 210 | S+A | 183 |
| | | | | 305 | | 325 | | 290 | | 205 | | 195 |
| | | | | 323 | | 340 | | 300 | | 200 | | 198 |

TABLE III-continued

Effect of combinations of metallic cations, Clofibrate and PDX chloride

|       |     |
|-------|-----|
|       | 297 |
| S+A+  |     |
| Mg    | 297 |
|       | 330 |
|       | 340 |
|       | 303 |
| S+A+  |     |
| Mg/   |     |
| Al    | 300 |
|       | 336 |

In the above Table:
 PL = placebo
 S = Secholex (15 g./day), PDX chloride
 Mg = magnesium hydroxide (2.4 g./day)
 Al = aluminum hydroxide (2.4 g./day)
 Mg/Al = combination of magnesium and aluminum hydroxides (2.4 + 2.4 g. = 4.8 g./day)
 A = clofibrate (1.5 g./day)
 S.Ch. = serum cholesterol level (mg./100 ml.) for each treatment The following Examples illustrate the compositions of the present invention.

EXAMPLE 1

Capsules

Aluminum hydroxide: 4 g.
Clofibrate: 2 g.

These ingredients were thoroughly mixed and formed into 0.75 g. capsules two of which were administered four times daily.

EXAMPLE 2

Capsules

Magnesium carbonate: 6 g.
Clofibrate: 1.5 g.

These ingredients were thoroughly mixed and formed into eight capsules, two of which were administered four times daily.

EXAMPLE 3

Mixture of a powder and micro-encapsulated liquid

Magnesium carbonate powder: 100 g.
ethyl para-chlorophenoxyisobutyrate (micro-encapsulated): 150 g.
flavouring: 5 g.
gum arabic powder: 25 g.

Because the ethyl ester has an unpleasant taste, it is conveniently mixed with the other components in the form of micro-capsules. The ethyl ester is micro-encapsulated to give a pore size of about 150 microns and then mixed with the other ingredients.

In this Example the ethyl para-chlorophenoxyisobutyrate may be replaced by an equal weight of n-propyl para-chlorophenoxyisobutyrate.

EXAMPLE 4

Oil suspension parachlorophenoxyisobutyric acid: 100 g.
magnesium carbonate: 100 g.
oil base: 1000 ml.

The above ingredients are mixed together for oral use. The oil base consists of equal parts of soya bean oil and purified linseed oil gelled with 1% by weight of aluminum monostearate. One teaspoonful is administered three times a day with meals.

EXAMPLE 5

Mixture with a third component which potentiates activity polyunsaturated phosphatidyl choline (from soya beans): 250 g.
ethyl para-chlorophenoxyisobutyrate: 250 g.
magnesium hydroxide: 250 g.
α-tocopherol acetate: 2.5 g.
mono- and di-glycerides: 120 g.
soya bean oil: 140 g.

The soya bean oil is mixed with the glyceride mixture and then poly-unsaturated phosphatidyl choline is dissolved with stirring and if necessary with heating in a water bath at 40°–50° C while protected by an inert gas, preferably also with exclusion of light. The α-tocopherol and ethyl ester were then added and the magnesium hydroxide worked in to give an oil suspension. The whole is then filled into hard gelatin capsules each containing 500 mg. Three capsules are given thrice daily with meals.

EXAMPLE 6

An emulsion cane sugar: 200 g.
sodium benzoate: 1 g.
pyridoxine HCl: 0.6 g.
aluminum hydroxide: 750 g.
polyethylene sorbitanmono-oleate condensate: 10 g.
ethyl p-chlorophenoxyisobutyrate: 500 g.
soya bean lecithin: 25 g.
mixed tocopherol: 2.4 g.
propyl gallate concentrate: 0.05 g.
water: 400 ml.

The cane sugar, sodium benzoate, pyridoxine and condensate are dissolved in the water and stirred into a mixture of the ester, lecithin, tocopherols and gallate. The aluminum hydroxide is then added and the resulting emulsion suspension is homogenised by passing through a conventional homogeniser. There is thus obtained an emulsion for oral administration for therapeutic purposes. About two teaspoonfuls (10 ml.) are given three or four times daily.

EXAMPLE 7

Mixture of anion exchange resin, clofibrate derivative and metallic salt as a powder Magnesium hydroxide: 40 g.
calcium salt of p-chlorophenoxyisobutyric acid: 100 g.
PDX chloride: 1000 g.
gum arabic: 300 g.

The finely powdered ingredients are mixed thoroughly. For oral use, the powder is well mixed with water, a suitable daily dose being 20 g. of the powder in three divided doses with meals.

In the above example the calcium salt of parachlorophenoxyisobutyric acid can be substituted by the corresponding magnesium, aluminum or bismuth salt. Magnesium hydroxide can be replaced by aluminum hydroxide or bismuth oxide. PDX chloride can be replaced by colestipol or cholestyramine.

EXAMPLE 8

Mixture of anion exchange resin, clofibrate derivative and metallic salt in tablets or capsules Calcium carbonate: 20 g.
Magnesium hydroxide: 80 g.
Aluminum salt of parachlorophenoxyisobutryic acid: 100 g.
PDX chloride: 200 g.

The above ingredients are well mixed and filled into soft gelatin capsules.

Alternatively, to form tablets, the following additional ingredients are added:

Talc: 10 g.
Calcium stearate: 10 g.

and the mixture formed into tablets. Three tablets (500 mg.) are swallowed four times daily with meals.

In the above example calcium carbonate can be substituted by aluminum hydroxide. The aluminum salt of para-chlorophenoxyisobutyric acid can be substituted by the free acid or by its ethyl ester or potassium or sodium salt. PDX chloride can be replaced by colestipol or cholestyramine.

We claim:

1. A pharmaceutical composition for use in the treatment per os of hypercholesterolemia, which comprises a hypocholesteremic effective amount of
   a. a compound selected from p-chlorophenoxyisobutyric acid, the methyl, ethyl, propyl or butyl ester thereof or a sodium, potassium, calcium, magnesium, aluminum, zinc, bismuth or iron salt thereof, and
   b. an ingestible non-toxic aluminum or magnesium salt capable of dissolution in human gastrointestinal juices, the total amount of non-toxic metal being from 3.2 to 90 equivalents per mole of p-chlorophenoxyisobutyric acid or ester or salt thereof.

2. A composition according to claim 1 wherein the total amount of non-toxic metal is from 4 to 15 equivalents per mole of p-chlorophenoxyisobutyric acid or ester or salt thereof.

3. A composition according to claim 1 wherein a non-toxic magnesium salt is employed with the p-chlorophenoxyisobutyric acid or ester or salt thereof.

4. A composition according to claim 1 wherein a non-toxic aluminum salt is employed with the p-chlorophenoxyisobutyric acid or ester or salt thereof.

5. A composition according to claim 1 wherein there is also present on or more ingestible non-toxic basic anion exchange resins, there being from 50 to 8000 grams of resin per mole of p-chlorophenoxyisobutyric acid or ester or salt thereof.

6. A composition according to claim 5 wherein the anion exchange resin is selected from cholestyramine, colestipol or poly-[2-(diethyl-amino)ethyl]polyglycerylene dextran hydrochloride.

7. A composition according to claim 1 comprising ethyl p-chlorophenoxyisobutyrate and magnesium hydroxide.

8. A composition according to claim 1 comprising ethyl p-chlorophenoxyisobutyrate and aluminum hydroxide.

9. A method for the treatment of hypercholesterolemia, in which there is administered to the patient per os a hypocholesteremic effective dose of a pharmaceutical composition comprising
   a. a compound selected from p-chlorophenoxyisobutyric acid, the methyl, ethyl, propyl or butyl ester thereof or a sodium, potassium, calcium, magnesium, aluminum, zinc, bismuth or iron salt thereof, and
   b. an ingestible non-toxic aluminum or magnesium salt capable of dissolution in human gastrointestinal juices, the total amount of non-toxic metal being from 3.2 to 90 equivalents per mole of p-chlorophenoxyisobutyric acid or ester or salt thereof.

10. A method according to claim 9 wherein the composition contains a total amount of non-toxic metal from 4 to 15 equivalents per mole of p-chlorophenoxyisobutyric acid or ester or salt thereof.

11. A method according to claim 9 wherein the composition contains a magnesium salt in combination with the p-chlorophenoxyisobutyric acid or ester or salt thereof.

12. A method according to claim 9 wherein the composition contains an aluminum salt in combination with the p-chlorophenoxyisobutyric acid or ester or salt thereof.

13. A method according to claim 9 wherein the composition also contains one or more ingestible non-toxic basic anion exchange resins, there being from 50 to 8000 grams of resin per mole of p-chlorophenoxyisobutyric acid or ester or salt thereof.

14. A method according to claim 13 wherein the anion exchange resin is selected from cholestyramine, colestipol or poly-[2-(diethyl-amino)ethyl]polyglycerylene dextran hydrochloride.

15. A method according to claim 9 wherein the composition comprises ethyl p-chlorophenoxyisobutyrate and magnesium hydroxide, said composition being administered in an amount sufficient to provide a daily dosage of about 1.5 g. of ethyl p-chlorophenoxyisobutyrate and about 2.4 g. of magnesium hydroxide.

16. A method according to claim 9 wherein the composition comprises ethyl p-chlorophenoxyisobutyrate and aluminum hydroxide, said composition being administered in an amount sufficient to provide a daily dosage of about 1.5 g. of ethyl p-chlorophenoxyisobutyrate and about 2.4 g. of aluminum hydroxide.

* * * * *